US006858727B2

(12) United States Patent
Lee et al.

(10) Patent No.: US 6,858,727 B2
(45) Date of Patent: Feb. 22, 2005

(54) INTERMEDIATE OF CARBAPENEM ANTIBIOTICS AND PROCESS FOR THE PREPARATION THEREOF

(75) Inventors: Cheol-hae Lee, Taejon (KR); Bong-jin Kim, Taejon (KR); Do-kyu Pyun, Taejon (KR); Won-jang Jeong, Pusan (KR); Jae-hak Kim, Taejon (KR); Hee-jung Chung, Taejon (KR); Hyun-jung Kwak, Pusan (KR); Eun-jung Kim, Taejon (KR); Shin-seup Song, Choongchungnam-do (KR); Yong-ho Chung, Kyunggi-do (KR)

(73) Assignees: Dong Wha Pharm, Ind. Co., Ltd., Seoul (KR); Korea Research Institute of Chemical Technology, Taejon (KR)

( * ) Notice: Subject to any disclaimer, the term of this patent is extended or adjusted under 35 U.S.C. 154(b) by 21 days.

(21) Appl. No.: 10/344,267

(22) PCT Filed: Aug. 6, 2001

(86) PCT No.: PCT/KR01/01327

§ 371 (c)(1),
(2), (4) Date: Feb. 10, 2003

(87) PCT Pub. No.: WO02/12230

PCT Pub. Date: Feb. 14, 2002

(65) Prior Publication Data

US 2003/0191106 A1 Oct. 9, 2003

(30) Foreign Application Priority Data

Aug. 10, 2000 (KR) ..................................... 2000/0046447

(51) Int. Cl.[7] ................. C07D 205/08; C07D 413/06; C07D 265/06; C07F 9/568; C07F 7/18

(52) U.S. Cl. ........................... 540/200; 544/71; 544/97

(58) Field of Search .......................................... 540/200

(56) References Cited

U.S. PATENT DOCUMENTS

| 5,442,055 A | 8/1995 | Iwasaki et al. |
| 5,631,363 A | 5/1997 | Iwasaki et al. |
| 5,847,115 A | 12/1998 | Iwasaki et al. |
| 6,011,150 A | 1/2000 | Iwasaki et al. |
| 6,340,751 B1 * | 1/2002 | Saito et al. ................. 540/200 |

FOREIGN PATENT DOCUMENTS

| EP | 0 126 587 | 5/1984 |
| JP | 62-252786 | 11/1987 |
| JP | 63-188662 | 8/1988 |
| JP | 64-025779 | 1/1989 |
| JP | 4-279588 | 5/1992 |
| JP | 07-082248 | 3/1995 |
| JP | 07-082249 | 3/1995 |

OTHER PUBLICATIONS

Fuentes, L.M. et al., "Lewis Acid Mediated Condensation of Chiral Imide Enolates: A General Approach to the Synthesis of Chiral Carbapenem Precursors," 108 J. Am. Chem. Soc. pp. 4675–4676 (1986).

Nagao, Yoshimitsu et al., "Highly Diastereoselective Alkylation onto 4–Acetoxy–2azetidinones Employing Tin (II) Enolates of C4–Chiral 3–Acyl–1,3–thiezolidine–2–thiones," 108 J. Am. Chem. Soc. pp. 4673–4675 (1986).

Shibata, Tomoyuki et al., "Synthetic Studies of 1–β–Methylcarbapenem Antibiotics," The Journal of Antibiotics pp. 374–381 (1989).

Remuzon, Phillippe et al., "Studies Toward the Stereocontrolled Synthesis of a Key Azetidinone–Acid Intermediate i the Preparation of a New Carbapenem," 51(35) Tetrahedron pp. 9657–9670 (1995) Great Britain.

Deziel, Robert et al., "Simple and Highly Diastereoselective Synthesis of a 1β–Methylcarbapenem Key Intermediate Involving Divalent Tin Enolates," 27(47) Tetrahedron Letters pp. 5687–5690 (1986) Great Britain.

Ito, Yoshio, et al., Highly Stereocontrolled Synthesis of the 1β–Methylcarbapenem Key Intermediate by the Reformatsky Reaction of 3–(2–Bromopropionyl)–2–Oxazolidone Derivatives with a 4–Acetoxy–2–Azetidinone[1]) 47(16/17) Tetrahedron pp. 2801–2820 (1991) Great Britain.

Ito, Yoshio, et al., "A Highly Stereoselective Synthesis of a Key Intermediate of 1β–Methylcarbapenems Employing the Reformatsky Reaction of 3–(2Bromopropionyl)–2–Oxazolidone Derivatives," 28(52) Tetrahedron Letters pp. 6625–6628 (1987) Great Britain.

Berks, Andrew H., "Preparation of Two Pivotal Intermediates for the Synthesis of 1β–Methyl Carbapenem Antibiotics," 52(2) Tetrahedron pp. 331–375 (1996) Great Britain.

* cited by examiner

Primary Examiner—Mark L. Berch
(74) Attorney, Agent, or Firm—Burns, Doane, Swecker & Mathis, L.L.P.

(57) ABSTRACT

There is disclosed an azetidinone compound of the formula (I):

(I)

wherein R is hydrogen, or a hydroxy protecting group, $R_1$ and $R_2$ are each independently alkyl of 1–15 carbon atoms, benzyl or cyclized together with the carbon atom to which they are attached to form a 5 or 6-membered cyclic hydrocarbon or a heterocyclic radical having one or two hetero ring atoms, said hetero ring atoms being selected from the group consisting of O and S; $R_3$ is lower alkyl or —COO (lower alkyl) $R_4$ is phenyl, or phenyl substituted with halogen, lower alkoxy or nitro which is useful as a synthetic intermediate to the 1'β-methylcarbapenem-type antibacterial agent.

5 Claims, No Drawings

INTERMEDIATE OF CARBAPENEM ANTIBIOTICS AND PROCESS FOR THE PREPARATION THEREOF

BACKGROUND OF THE INVENTION

1. Field of the Invention

This invention relates to a novel azetidinone compound of the following general formula (I), which is useful as an intermediate of β-methylcarbapenem antibiotics and its preparing process:

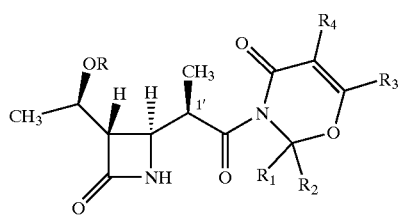
(I)

wherein, R is a hydrogen atom or a protecting group of hydroxy; $R_1$ and $R_2$ are independently $C_1$–$C_{15}$ alkyl, benzyl or cyclized to be 5 or 6-membered ring which is cyclic hydrocarbon or heterocyclic compound containing at least one of O and S; $R_3$ is a lower alkyl or a lower alkyl ester; $R_4$ is benzene or benzene substituted with halogen atom, a lower alkoxy or nitro; and, the methyl group in 1' position is R configuration, which is expressed by β-methyl in all general formula hereunder.

Further, this invention relates to a process for preparing a novel azetidinone compound of the general formula (I) by reacting 4-acetoxy-azetidinone compound of the general formula (II) with α-halopropionamide compound of the general formula (III):

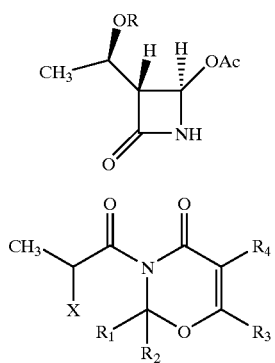
(II)

(III)

wherein R, $R_1$, $R_2$, $R_3$ and $R_4$ are the same as defined above; and, X is a halogen atom.

Further, this invention relates to α-halopropionamide compound of the general formula (III), a novel stereoselective additive.

The general formula (I) compound with better stereoselectivity may be made available using the general formula (III) compound.

Further, this invention relates to α-halopropionamide compound of the novel general formula (III) by reacting monocyclic compound of the general formula (VIII) with 2-halopropionic acid of the general formula (IX) or its activated complex.

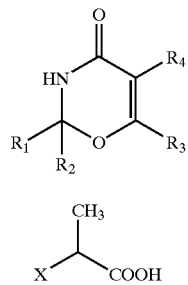
(VIII)

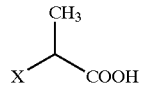
(IX)

wherein $R_1$, $R_2$, $R_3$, $R_4$, and X are the same as defined above.

Further, this invention relates to a novel process for preparing β-methylcarbapenem ester compound of the general formula (V).

More specifically, the general formula (V) compound may be made available in a manner such that N-substituted azetidinone compound of the general formula (XI), so obtained by reacting the general formula (I) compound with haloacetate compound of the general formula (X), is further under cyclization and esterification in situ.

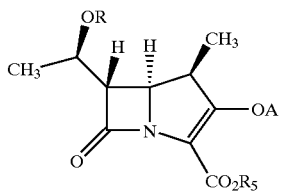
(V)

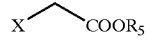
(X)

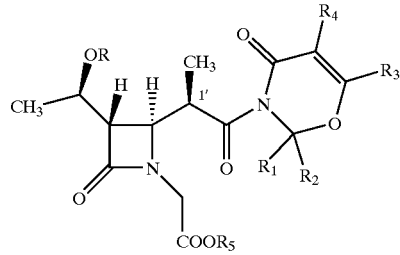
(XI)

wherein R, $R_1$, $R_2$, $R_3$, $R_4$, and X are the same as defined above. $R_5$, which is a protecting group of carboxyl to be easily removed by the common process, includes a lower alkyl, a lower alkenyl, a halogeno-lower alkyl, nitrobenzyl, a lower alkoxy-benzyl or benzhydryl; OA, which is an esterified hydroxy group which can be easily substituted by —S—$R_6$ ($R_6$ is the corresponding heterocyclic compound exhibiting antibiotic activity), includes —OP(O)(O$R_7$)$_2$ ($R_7$ is aryl or a lower alkyl), a substituted or unsubstituted lower alkylsulfonyl (e.g., methanesulfonyl, ethanesulfonyl, trifluoromethanesulfonyl), aryloxycarbonyl (e.g., benzyloxycarbonyl) and among them, it is preferred to employ some esterified hydroxyl groups selected from diarylphosphoryloxy, di-lower alkyl phosphoryloxy, a substituted or unsubstituted lower alkylsulfonyl, substituted or unsubstituted arylsulfonyl.

Further, this invention relates to a novel process for preparing 1'β-methylazetidinone compound of the general formula (IV).

More specifically, the general formula (IV) compound may be made available via hydrolysis of the general formula (I) compound.

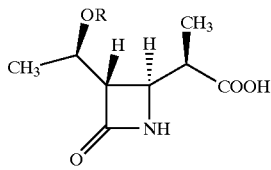
(IV)

wherein R is the same as defined above.

2. Description of the Related Art

β-methylcarbapenem antibiotic of the following general formula (XII) has a wide spectrum of antibiotic activity against Gram-negative bacteria including Pseudomonas aeruginosa and Gram-positive bacteria as well as penicillin- or cephalosporin-resistant bacteria.

The typical examples of β-methylcarbapenem antibiotic include meropenem (Europe Publication Patent No. 126587) and biapenem (Japan Publication Patent Pyung 1-25779), and a number of other β-methylcarbapenem antibiotic has been under development.

The currently known synthesis process for the preparation of β-methylcarbapenem antibiotic are made available through the following two processes.

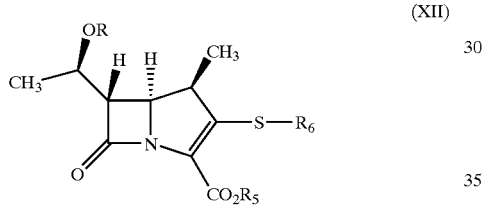
(XII)

wherein R and $R_5$ are the same as defined above; and $R_6$ is a heterocyclic compound exhibiting an antibiotic activity.

The first process comprises the steps of:

(1) generating β-methylazetidinone compound of the general formula (IV) is prepared using 4-acetoxy-azetidinone compound of the general formula (II) as starting material in the presence of diverse stereoselective additives; and, (2) preparing the general formula (V) compound, a final intermediate of carbapenem antibiotic, from the general formula (IV) compound via 5 or 6 steps, followed by preparing β-methylcarbapenem antibiotic of the general formula (XII). Now that the process for preparing the general formula (V) compound, a final intermediate of carbapenem antibiotic from the general formula (IV) compound has been well disclosed in Japan Publication Patent Sho 63-188662, this invention does not discussed such process in detail.

The introduction of 1'β-methyl group in the aforementioned reactions in Aldol-type has been known with better stereoselectivity, but a variety of reagents used for these reactions, including tin triplate, titanium chloride or dibutylboron triplate, are uneasy to be handled and expensive, thus making it difficult to ensure the large-scale production of β-methylcarbapenem antibiotics.

Some similar process has been disclosed in a number of literatures (Japan Publication Patent No. 87-252786): J.A.C.S. vol. 108, pp. 4675–4676, 1986: same journal vol. 108, pp. 4673–4675, 1986: J. Antibiotics, pp. 374, 1989, Tetrahedron, pp. 9657, 1995: Terahedron Letters, vol. 27, pp. 5687, 1986).

Such process, which is designed to synthesize the general formula (V) compound, a final intermediate of carbapenem antibiotic from the general formula (IV) compound via 5 or 6 steps, proven to have better yield in each process step but requires a longer time in the whole preparing process.

The second process developed by Tanabe Co. of Japan is designed to improve some shortcomings encountered with the first process.

More specifically, the second process comprises the steps of:

(1) generating 1'β-methyl intermediate of the following general formula (VII) in Reformatsky reaction using 4-acetoxy-azetidinone compound of the general formula (II) as starting material in the presence of stereoselective additive of the general formula (VI) to easily handle zinc or magnesium; and, (2) hydrolyzing the general formula (VII) compound to obtain either general formula (IV) compound of the first process, or to generate the general formula (V) compound from the general formula (VII) compound via N-alkylation, cyclization and esterification (Korea Patent Registration No. 10-231223), followed by preparing 1β-merhylcarbapenem antibiotic of the general formula (XII).

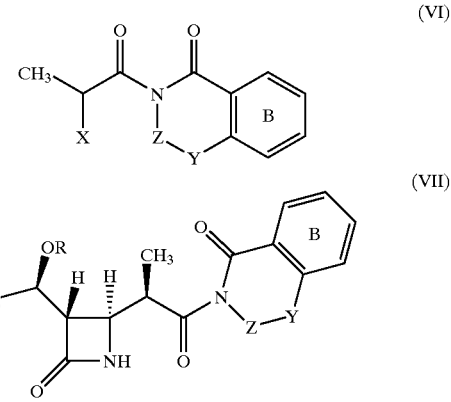

wherein R is the same as defined as above; Z is $C_3$–$C_7$ alkenyl, $C_{1-20}$ alkyl, or methylene substituted with two groups selected from one group of aralkyl; Y is an oxygen atom, an sulfur atom, methylene or amine; and ring B is a benzene ring substituted with a halogen atom, a lower alkyl, or a lower alkoxy.

It has been reported that the second process is industrially more advantageous than the first process in terms of easier reaction steps and conditions.

Some similar process have been disclosed in a number of literatures (e.g., Tetrahedron pp. 2801, 1991: Tetrahedron Letters, 6625 pp, 1987: Japan Publication Patent Gazette Pyung 7-82248: same Gazette Pyung 7-82249).

β-methylcarbapenem antibiotic of the general formula (XII) may be made available through the well known process (e.g., Japan Publication Patent Pyung 4-279588) by reacting the general formula (V) compound with some heterocyclic thiol compound.

Nevertheless, the second process has recognized some disadvantage in terms of poor stereoselectivity.

SUMMARY OF THE INVENTION

An object of this invention is to provide an intermediate of β-methylcarbapenem stereoselectively, wherein an intermediate of 1'β-methylcarbapenem is prepared in Reformatsky reaction using α-halopropionamide of the general formula (III), a novel stereoselective additive, thus ensuring more increasing rate of 1'β-methyl group versus 1'α-methyl group than the prior art.

This invention relates to a novel azetidinone compound of the following general formula (1), which is useful as an intermediate of β-methylcarbapenem antibiotics and its preparing process:

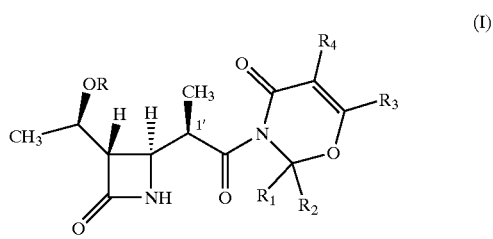

(I)

wherein R, $R_1$, $R_2$, $R_3$ and $R_4$ are the same as defined above.

The examples of the protecting group of R include a lower alkoxycarbonyl, tri-lower alkylsilyl, quartenary-butyl-dimethylsilyl, benzyloxycarbonyl or 4-nitrobenzyloxycarbonyl.

The most preferred compound from the general formula (I) compound is comprised, wherein R is quartenary-butyl-dimethylsilyl; $R_1$ and $R_2$ is cyclized to form cyclohexyl; $R_3$ is methyl ester; and, $R_4$ is benzene ring.

The examples of the salts of general formula (I) azetidinone compound include inorganic and organic acid addition salts. According to this invention, the examples of inorganic acid addition salts include hydrochloride, hydrobromide or sulfate. The examples of organic acid salts include acetate, oxalate, tartrate, fumarate, maleate or benzenesulfonate.

Further, azetidinone compound (I) may contain stereoisomers of β-methyl group (R configuration) and α-methyl group (S configuration) in 1' position.

The process for preparing the general formula (I) compound is prepared by reacting 4-acetoxy-azetidinone compound of the following general formula (II) with α-halopropionamide compound of the following general formula (III).

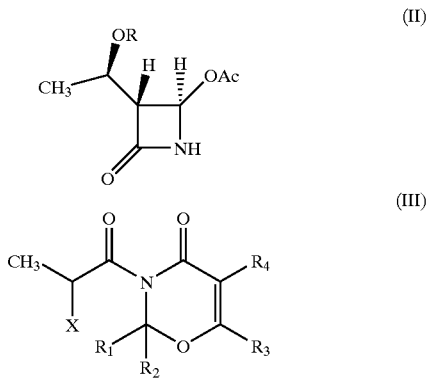

wherein $R_1$, $R_2$, $R_3$, $R_4$, and X are the same as defined above.

The reaction between α-halopropionamide (III) and azetidinone compound (II) may be performed using some metals employed in Grignard reaction among nonpolar solvents or some metals which can form a metal complex with the general formula (III) compound as steroselective additive. The examples of metals used for this invention include zinc or magnesium. The reaction solvents may be employed from the group consisting of tetrahydrofuran, toluene, xylene, dimethylformamide, and dimethylsulfoxide.

α-halopropionamide compound of the general formula (III) is employed to 1 mol of the general formula (II) compound in the amount of 1~3 mols, preferably in the amount of 1.2~1.7 mols. Some metals such as zinc may be employed in the amount of 2~4 mols. In the case of using magnesium, methyl iodide or 1,2-dibromoethane is added to the general formula (III) compound to prepare Grignard compound beforehand and then, the aforementioned reaction is performed. Such reaction is performed at the temperature of −10~100° C. In particular, the reaction using zinc is preferably performed at the temperature of 50~80° C., while the reaction using magnesium is performed at the temperature of 0~30° C. The use of Lewis acid catalyst (e.g., zinc bromide, triethylboran, trimethylsilyl chloride or magnesium bromide) in the amount of 0.01~1 mol in the reaction may facilitate the reaction, thus shortening the reaction time.

Further, this invention relates to α-halopropionamide compound of the general formula (III), a novel stereoselective additive.

The general formula (I) compound with better stereoselectivity may be made available using the general formula (III) compound.

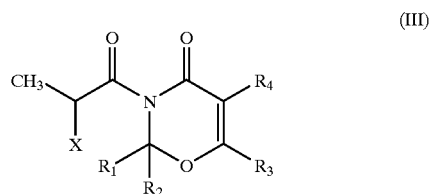

(III)

wherein $R_1$, $R_2$, $R_3$, $R_4$, and X are the same as defined above.

Further, this invention relates to a process for preparing α-halopropionamide compound of the novel general formula (III) by reacting monocyclic compound of the general formula (VIII) with 2-halopropionic acid of the general formula (IX) or its activated complex.

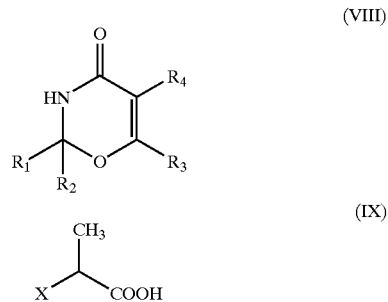

wherein $R_1$, $R_2$, $R_3$, $R_4$, and X are the same as defined above.

The reaction between monocyclic compound of the general formula (VIII) and 2-halopropionic acid of the general formula (IX) is performed in the presence of dehydrating agent from nonpolar solvents. The examples of nonpolar solvents include ethylether, dichloromethane, chloroform, benzene, toluene, tetrahydrofuran or acetonitrile. The examples of dehydrating agents also include carbonyldiimidazole, dicyclocarbodiamide or 1-hydrobenzimidazole. The reaction is performed at the temperature of −10~50° C., preferably at the temperature of 0~25° C.

Further, α-halopropionamide compound of the novel general formula (III) may be prepared by reacting monocyclic compound of the general formula (VIII) with the activated complex of 2-halopropionic acid such as acid halide or mixed acid anhydride in the presence of base. The solvent may be selected from the aforementioned reaction. The examples of base include alkali metal, a lower alkyl lithium, pyridine or di-lower alkylaniline. The reaction is preferably at the temperature of −20~30° C.

Further, this invention relates to a novel process for preparing β-methylcarbapenem ester compound of the general formula (V).

More specifically, the general formula (V) compound may be made available in a manner such that N-substituted azetidinone compound of the general formula (XI), so obtained by reacting the general formula (I) compound with haloacetate compound of the general formula (X), is further under cyclization and esterification in situ.

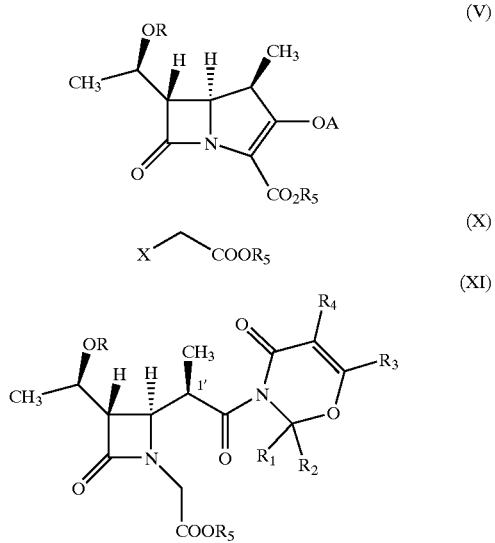

wherein R, $R_1$, $R_2$, $R_3$, $R_4$, $R_5$ X and OA are the same as defined above.

The reaction between the general formula (I) compound and the general formula (X) compound is performed using nonpolar solvent in the presence of base.

The examples of base include 1,8-diazabicyclo[5.4.0] undec-7-ene as organic base; alkali metal hydride, alkali metal hydroxide or alkali metal carbonate as alkali metal base; and, sodium amide, lithium diisopropylamide, sodium bis(trimethylsilyl)amide as amine metal salt. The examples of solvent include tetrahydrofuran, benzene, toluene, dichloromethane. The reaction is performed at the temperature of −50~−20° C.

The general formula (XI) compound, so obtained by reacting the general formula (I) compound with the general formula (X) compound, is further under cyclization and esterification in situ to afford the general formula (V) compound.

The cyclization of N-substituted azetidinone compound of the general formula (XI) is performed in the presence of base. The base used in the cycliazation may be selected from Dieckmann-type reaction, and the examples of base include alkali metal salts such as sodium bis(trimethylsilyl)amide or lithum bis(trimethylsilyl)amide. The base is employed to the general formula (XI) compound in the amount of 1.0~3.0 equivalents, preferably in the amount of 2.0~2.5 equivalents.

The examples of solvent include in the reaction include tetrahydrofuran, ethylether, dioxane, toluene or benzene. The reaction is performed at the temperature of −78~50° C., preferably at the temperature of −60~10° C. During the reaction, enolate salt of the general formula (XIII) is generated but the esterification is continued without separating the salt.

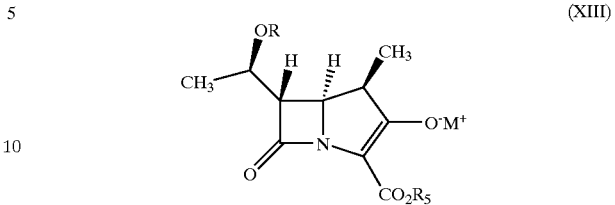

wherein R and $R_5$ are the same as defined above; and, $M^+$ is alkali metal ion.

The esterification of hydroxy salt of the general formula (XIII) compound so, generated from intramolecular cyclization is further proceeded with the addition of activated complex. The examples of activated complex include acid chloride or acid anhydride such as di-arylphosphate (e.g., diphenylphosphate) or di-lower alkylphosphate (e.g., diethylphosphate). Further, the activated complex of esterified agent in the reaction to the general formula (XI) compound in the amount of 1.0~4.0 equivalents, preferably in the amount of 2.0~3.0 equivalents.

The reaction is preferably performed at the temperature of −78~30° C., more preferably at the temperature of −60~10° C.

After the intramolecular cyclization, the next esterification may be continued with the addition of base and silylated material in order. The examples of silylated material include trimethylsilyl choride, t-butyldimethylsilyl chloride or tetrachlorosilane.

The use of 4-dimethylaminopyridine in the esterification as reaction catalyst may shorten the reaction time. Such catalyst may be employed to the general formula (XI) compound in the amount of 0.01~0.5 equivalents, preferably in the amount of 0.05~0.1 equivalents. During the intramolecular cyclization, the general formula (VIII) compound is generated as by-product but its recycling into the general formula (III) compound as stereoselective additive after recovery.

Further, this invention relates to a novel process for preparing 1'β-methylazetidinone compound of the general formula (IV).

More specifically, the general formula (IV) compound may be made available via hydrolysis of the general formula (I) compound.

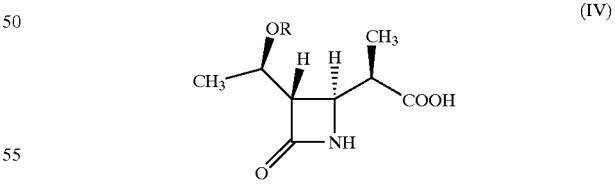

wherein R is the same as defined above.

The hydrolysis of the general formula (I) compound may be performed in the presence of hydrogen peroxide and metal salt hydroxide using nonpolar solvent. The examples of solvent include water and dioxane, tetrahydrofuran, dimethylformamide or methylalcohol; hence, it is preferred to employ water and tetrahydrofuran. The examples of metal salt hydroxide include lithium hydroxide, sodium hydroxide or potassium hydroxide; hence, it is preferred to employ lithium hydroxide. Hydrogen peroxide is employed to the general formula (I) compound in the amount of 1~10 equivalents, preferably in the amount of 6~8 equivalents. Metal salt hydroxide is employed to the general formula (I) compound in the amount of 1~5 equivalents, preferably in the amount of 2~3 equivalents. The reaction is preferably performed at the temperature of −5~5° C.

From the abbreviated definitions described in the Detailed Description of the Invention and claims, the definitions "a lower alkyl", "a lower alkoxy" and "a lower alkylene" refer to linear or branched chain having 1 to 4 carbons, respectively; and, the definition "a lower alkenyl" means a linear chain having 2 to 5 carbons.

Hereunder is given a more detailed description of the present invention using examples and comparative examples. However, it should not be construed as limiting the scope of the present invention.

DETAILED DESCRIPTION OF THE INVENTION

Preparation Example 1

Preparation of methyl 3-cyano-3-phenylpyruvic acid ester 12 g of metal sodium (or a same equivalent of sodium methoxide) was slowly added to 46.8 g of phenylacetonitrile dissolved in 200 ml of dried methylalcohol. Hence, the temperature was increased by 50° C. due to exothermic reaction. 47.2 g of dimethyloxalate was added to the mixture at the same temperature, cooled down to room temperature and stirred for 18 hours at room temperature. The reacting solution was cooled down by ice water and with the addition of 200 ml of 2N-sulfuric acid solution and then, methanol solvent only was concentrated under reduced pressure. The residue was extracted by ethyl acetate two times and dried over $MgSO_4$, while the solvent was concentrated under reduced pressure. Normal hexane was added to a yellow crystal, so obtained, and after being filtered off, the residue was dried under vacuum to obtain 66.6 g of a desired compound (yield: 82%). mp 112~114° C.; $^1$H-NMR(CDCl$_3$, 200 MHz) δ 1.25–1.78(s, 8H), 2.04–2.27(m, 5H), 3.58(s, 3H), 6.99 (bs, 1H), 7.25–7.37(m, 5H); IR(CHCl$_3$) 1242, 1402, 1736, 2939, 3070, 3200 cm$^{-1}$.

Preparation Example 2

Preparation of ethyl 3-cyano-3-phenylpyruvic acid ester

The reaction was performed in the same manner as Preparation example 1 except for using diethyloxalate instead of dimethyloxalate and ethanol as a reaction solvent, thus obtaining a desired compound in a yellow crystals (yield: 75%). mp 95~97° C.; $^1$H-NMR(CDCl$_3$, 200 MHz) δ 1.51(t, J=7.2 Hz, 3H), 4.53(AB–q, J=7.2 Hz, 2H), 7.26–7.48 (m, 3H), 7.66–7.92(m, 2H); MS(70 ev, m/e) 217(M$^+$), 193, 111.

Preparation Example 3

Preparation of methyl 3-cyano-3-(4-chlorophenyl) pyruvic acid ester

The reaction was performed in the same manner as Preparation example 2 except for using 4-chlorophenyl-acetonitrile instead of phenylacetonitrile, thus obtaining a desired compound in a yellow crystals (yield: 82%). mp 105~107° C.; $^1$H-NMR(CDCl$_3$, 200 MHz) δ 4.20(s, 3H), 7.49(d, J=7.6 Hz, 2H), 7.91(d, J=7.8 Hz, 2H); MS(70 ev, m/e) 237(M$^+$), 183, 135.

Preparation Example 4

Preparation of methyl 3-cyano-3-(4-methoxyphenyl) pyruvic acid ester

The reaction was performed in the same manner as Preparation example 2 except for using 4-methoxyphenylacetonitrile instead of phenylacetonitrile, thus obtaining a desired compound in a yellow crystals (yield: 87%). mp 125~127° C.; $^1$H-NMR(CDCl$_3$, 200 MHz) δ 3.77(s, 3H), 4.00(s, 3H), 6.85(d, J=9.2 Hz, 2H), 7.76(d, J=9.2 Hz, 2H); MS(70 ev, m/e) 233(M$^+$), 173, 145.

Preparation Example 5

Preparation of methyl 3-cyano-3-(4-nitrophenyl) pyruvic acid ester

The reaction was performed in the same manner as Preparation example 2 except for using 4-nitrophenylacetonitrile instead of phenylacetonitrile, thus obtaining a desired compound in a bright yellow crystals (yield: 35%). mp 135~137° C.; $^1$H-NMR(CDCl$_3$, 200 MHz) δ 3.82(s, 3H), 7.48(d, J=8.62 Hz, 2H), 8.18(d, J=8.8 Hz, 2H); MS(70 ev, m/e) 248(M$^+$).

Preparation Example 6

Preparation of methyl 4-oxo-3-phenyl-1-oxa-5-azaspiro[5.5]undec-2-en-2-carboxylic acid ester (the General Formula (VIII) Compound)

52.5 g of methyl 3-cyano-3-phenylpyruvic acid ester was added to 97 ml of glacial acetic acid, followed by the addition of 29.4 g of cyclohexanone and 32.7 ml of anhydrous acetic acid in order at 10° C. With the slow addition of 48 ml of concentrated sulfuric acid dissolved in 97 ml of glacial acetic acid at the same temperature, the reacting solution was stirred for 2 hours by gradually increasing the temperature to room temperature. The reacting solution was cooled down and with the addition of 100 ml of water, stirred for 10 minutes. The precipitation, so formed, was filtered off and washed with a mixing solution (normal hexane: ethyl acetate=1:1) and hexane, respectively. The residue was dried under vacuum to obtain 67 g of a pure desired compound in a pale yellow solid (yield: 82%). mp 170~172° C.; $^1$H-NMR(CDCl$_3$, 200 MHz) δ 3.89(s, 3H), 7.22–7.26(m, 5H), 7.77(d, 1H); IR(CHCl$_3$) 1438, 1719, 2224, 3191 cm$^{-1}$.

Preparation Example 7–14

Preparation of the General Formula (VIII) Compound

As outlined in the following table 1, the compounds were prepared in a manner such that each compound, so prepared by Preparation examples and ketone compounds were reacted by Preparation example 6.

TABLE 1

(VIII)

[Structure: 6-membered ring with HN, C=O, $R_4$, $R_3$, O, $R_2$, $R_1$]

| Preparation examples | $R_1$ | $R_2$ | $R_3$ | $R_4$ | Yield (%) | Property (mp, °C.) |
|---|---|---|---|---|---|---|
| 7 | —CH₃ | —CH₃ | —CO₂CH₃ | -Ph | 52 | mp 85–88 |
| 8 | n-C₄H₉ | n-C₄H₉ | —CO₂CH₃ | -Ph | 32 | mp 73–75 |
| 9 | —CH₂Ph | —CH₂Ph | —CO₂CH₃ | -Ph | 43 | mp 105–107 |
| 10 | —(CH₂)₅— | | —CO₂CH₃ | -C₆H₄-OCH₃ | 82 | mp 167–169 |
| 11 | —(CH₂)₅— | | —CO₂CH₃ | -C₆H₄-Cl | 88 | mp 148–149 |
| 12 | —(CH₂)₅— | | —CO₂CH₃ | -C₆H₄-NO₂ | 25 | mp 171–172 |
| 13 | —(CH₂)₅— | | —CO₂Et | -Ph | 81 | mp 139–141 |
| 14 | tetrahydropyran | | —CO₂CH₃ | -Ph | 66 | mp 117–119 |

EXAMPLE 1

Preparation of methyl 5-(2-bromopropionyl)-4-oxo-3-phenyl-1-oxa-5-azaspiro[5.5]undec-2-en-2-carboxylic c acid ester (the General Formula (III) Compound)

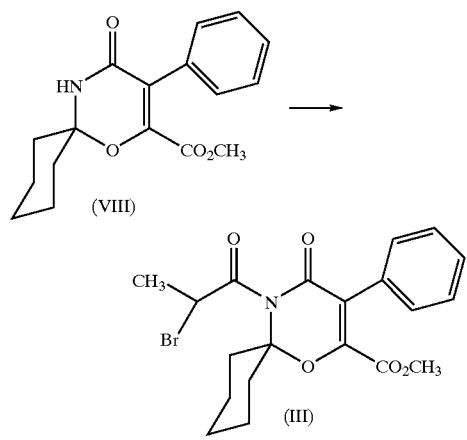

12.2 g of methyl 4-oxo-3-phenyl-1-oxa-5-azaspiro[5.5]undec-2-en-2-carboxylic acid ester was dissolved in 60 ml of anhydrous tetrahydrofuran and after being cooled down to −10° C., 4.26 ml of pyridine and 5.52 ml of 2-bromoacetyl bromide were slowly added to the above mixture. The reacting solution was stirred at room temperature for 6 hours and then, the reaction was terminated. The reacting solution was diluted with water and extracted two times by 100 ml of ethyl acetate each. The collected organic layer was washed with 10% sodium bicarbonate solution, dried over $MgSO_4$ and concentrated under reduced pressure. After 50 ml of isopropylalcohol was added to the residue, the mixture was stirred for a short time and then, crystals were formed. The crystals, so formed, filtered off and washed with 10 ml of isopropylalcohol each two times. After being washed with normal hexane, the residue was dried under vacuum to obtain 16.1 g of a desired compound in pale yellow solid (yield: 92%). mp 104~105° C.; $^1$H-NMR(CDCl₃, 200 MHz) δ 1.11–12.66(m, 10H), 1.84(d, J=6.6 Hz, 3H), 3.64(s, 3H), 5.06(q, J=6.8 Hz, 1H), 7.21–7.41(m, 5H); IR(CHCl₃) 1384, 1445, 1675, 1631, 1735, 2866, 2940 cm⁻¹.

EXAMPLES 2–9

Preparation of the General Formula (III) Compound

The corresponding starting material and 2-bromoacetylbromide were reacted by the same process of Example 1, thus preparation the compounds listed in the following table 2.

TABLE 2

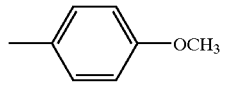

| Examples | R₁ | R₂ | R₃ | R₄ | Yield (%) | Property (mp, °C.) |
|---|---|---|---|---|---|---|
| 2 | —CH₃ | —CH₃ | —CO₂CH₃ | -Ph | 76 | Oily material |
| 3 | n-C₄H₉ | n-C₄H₉ | —CO₂CH₃ | -Ph | 73 | Oily material |
| 4 | —CH₂Ph | —CH₂Ph | —CO₂CH₃ | -Ph | 55 | Oily materia |
| 5 | —(CH₂)₅— | | —CO₂CH₃ | 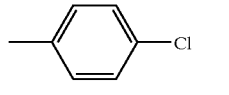 | 95 | Oily material |
| 6 | —(CH₂)₅— | | —CO₂CH₃ | 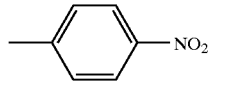 | 93 | Cotton shape |
| 7 | —(CH₂)₅— | | —CO₂CH₃ | 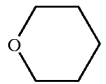 | 88 | mp 75° C. |
| 8 | —(CH₂)₅— | | —CO₂Et | -Ph | 86 | Oil material |
| 9 | 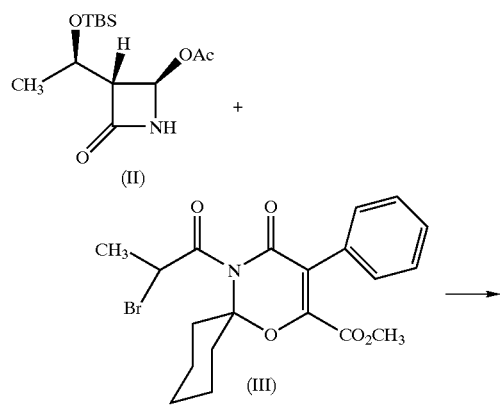 | | —CO₂CH₃ | -Ph | 84 | mp 117–119° C. |

EXAMPLE 10

Preparation of methyl 5-{(2R)-2-[(3S, 4R)-3-[(1R)-1-t-butyldimethylsilyloxyethyl]-2-oxo-azetidine-4-yl]propionyl}-4-oxo-3-phenyl-1-oxa-5-azaspiro[5.5]undec-2-en-2-carboxylic acid ester (the General Formula (I) Compound)

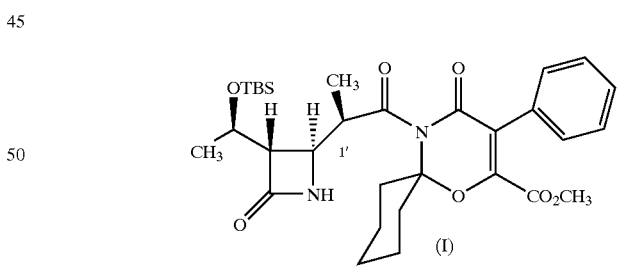

5 g of (3R, 4R)-4-acetoxy-3-[(1R)-1-t-butyldimethyl-silyloxyethyl]-2-azetidinone was dissolved in 60 ml of anhydrous tetrahydrofuran and with the addition of 3.41 g of zinc powder, the mixture was refluxed for 20 minutes. The reacting solution was cooled down to room temperature and then, 8.33 g of methyl 5-(2-bromopropionyl)-4-oxo-3-phenyl-1-oxa-5-azaspiro[5.5]undec-2-en-2-carboxylic acid ester dissolved in 20 ml of anhydrous tetrahydrofuran was slowly added to the reacting solution. The solution was reheated and refluxed for 2 hours. The reacting solution was cooled down to room temperature and with the addition of phosphate buffer solution (pH=7.0), the insoluble material, so formed, was filtered off. The remaining solution was extracted with ethyl acetate two times. After the organic layer was dried over $MgSO_4$, the residue was purified on silica gel column chromatograpy (elute; ethyl acetate: hexane=1:4) to obtain compound 9.92 g of a desired compound (yield: 97%).

From the desired compound, so obtained, a mixture of stereoisomer 1'R and 1'S was present in 1' position expressed by the above scheme, and as a result of analysis by HPLC (Capcll park C-18 column, elute; acetonitrile: water=7:3), the ratio between 1'R isomer: 1'S isomer was 95:5. mp 68~70° C.; $^1$H-NMR(CDCl$_3$, 200 MHz) δ 0.00(s, 6H), 0.80(s, 9H), 1.11(d, J=6.4 Hz, 3H), 1.16(d, J=7.0 Hz, 3H), 1.52–1.81(m, 6H), 2.02–2.41(m, 4H), 2.79–2.82(m, 1H, 1'S-H), 3.12–3.16(m, 1H, 1'R-H), 3.12–3.16(m, 1), 3.37–3.44(m, 1H), 3.57(s, 3H), 3.85–3.89(m, 1H), 5.09(s, 1H), 7.13–7.21(m, 2H), 7.25–7.35(m, 3H); IR(CHCl$_3$) 1377, 1447, 1633, 1678, 1758, 2857, 2949 cm$^{-1}$.

EXAMPLES 11–16

Preparation of the General Formula (I) Compound

The corresponding starting material and (3R, 4R)-4-acetoxy-3-[(1R)-1-t-butyldimethylsilyloxyethyl]-2-azetidinone were reacted by the same process of Example 10, thus preparing the compounds listed in the following table 3.

EXAMPLE 17

Preparation of methyl 5-{(2R)-2-[(3S, 4R)-3-[(1R)-1-t-butyldimethylsilyloxyethyl]-2-oxo-azetidine-4-yl]propionyl}-4-oxo-3-phenyl-1-oxa-5-azaspiro[5.5]undec-2-en-2-carboxylic acid ester (the General acid ester (the General Formula (I) Compound)

As another process for preparing the compound of Example 10, a small amount of iodine was added to 15 mg of anhydrous tetrahydrofuran and with the addition of 655 mg of magnesium piece, 1.13 g of 1,2-dibromoethane was slowly added to the mixture. The temperature of the reacting solution was increased to reflux temperature due to exothermal reaction. Then, 2.26 g of 1,2-dibromoethane dissolved in 4.5 ml of tetrahydrofuran was slowly added to the solution and refluxed for 30 minutes. After the mixture was cooled down to 5° C., 1.72 g of (3R, 4R)-4-acetoxy-3-[(1R)-1-t-butyldimethylsilyloxyethyl]-2-azetidinone and 2.88 g of methyl 5-(2-bromopropionyl)-4-oxo-3-phenyl-1-oxa-5-azaspiro[5.5]undec-2-en-2-carboxylic acid ester dissolved in 8 ml of tetrahydrofuran were slowly added to the mixture. The reacting solution was stirred at 10° C. for 1 hour and with the addition of 90 ml of saturated ammonium chloride, the reaction was terminated and extracted with ethyl acetate. The extract was washed with brine, dried over $MgSO_4$ and concentrated under reduced pressure. The residue was purified on silica gel column chromatography (elute; ethyl acetate: hexane=1:4) to obtain 3.07 g of a desired compound (yield: 88%). This compound was the same as Example 2 and as a result of HPLC (the same conditions as Example 10), the ratio of 1'R-isomer:1'S-isomer was 98:2.

TABLE 3

| Examples | $R_1$ | $R_2$ | $R_3$ | $R_4$ | Yield (%) | Ratio of 1'R:1'S |
|---|---|---|---|---|---|---|
| 11 | n-$C_4H_9$ | n-$C_4H_9$ | —$CO_2CH_3$ | -Ph | 49.2 | 98:2 |
| 12 | —$CH_2Ph$ | —$CH_2Ph$ | —$CO_2CH_3$ | -Ph | 35 | 96:4 |
| 13 | —$(CH_2)_5$— | | —$CO_2CH_3$ | -C$_6$H$_4$-OCH$_3$ | 86 | 92:8 |
| 14 | —$(CH_2)_5$— | | —$CO_2CH_3$ | -C$_6$H$_4$-Cl | 88 | 97:3 |
| 15 | —$(CH_2)_5$— | | —$CO_2CH_3$ | -C$_6$H$_4$-NO$_2$ | 20 | 95:5 |
| 16 | —$(CH_2)_5$— | | —$CO_2Et$ | -Ph | 85 | 98:2 |

EXAMPLE 18

Preparation of methyl 5-{(2R)-2-[(3S, 4R)-1-allyloxycarboxylmethyl-3-[(1R)-1-t-butyldimethylsilyloxyethyl]-2-oxo-azetidine -4-yl]propionyl}-4-oxo-3-phenyl-1-oxa-5-azaspiro[5.5]undec-2-en-2-carboxylic acid ester (the General Formula (XI) Compound)

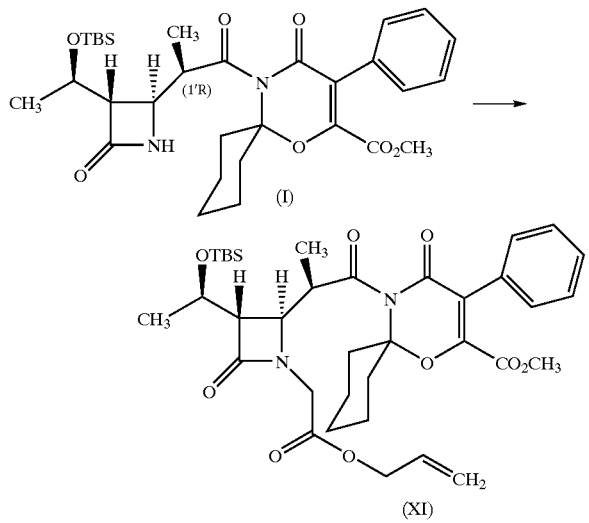

5.0 g of methyl 5-{(2R)-2-[(3S, 4R)-3-[(1R)-1-t-butyldimethylsilyloxyethyl]-2-oxoazetidine-4-yl]propionyl}-4-oxo-3-phenyl-1-oxa -5-azaspiro[5.5]undec-2-en-2-carboxylic acid ester was dissolved in 50 ml of anhydrous tetrahydrofuran and cooled down to −60° C. Under the atmosphere of nitrogen gas, 1.53 g of allylbromoacetate and 9.76 ml of sodium bis(trimethylsilyl)amide (1 mol of tetrahydrofuran solution) were slowly added to the mixture. The reacting solution was stirred at the same temperature for 15 minutes and with the gradual increase of temperature, the solution was further stirred at −30° C. for 40 minutes. After water was added to the reacting solution, the solution was extracted with ethyl acetate, dried over MgSO$_4$ and concentrated under reduced pressure. The residue was purified on silica gel column chromatography (elute; ethyl acetate: hexane=1:4) to obtain 4.89 g of oily desired compound (yield: 88%). $^1$H-NMR(CDCl$_3$, 200 MHz) δ 0.08(s, 6H), 0.86(s, 9H), 1.24(d, J=4.0 Hz, 3H), 1.27(d, J=3.0 Hz, 3H), 1.62–2.24(m, 10H), 3.01(dd, J=7.6, 2.0 Hz, 1H), 3.43–3.58(m, 1H), 3.63(s, 3H), 3.88–4.01(m, 2H), 5.21–5.39(m, 2H),580–6.01(m, 1H), 7.19–7.39(m, 5H); IR(CHCl$_3$) 1377, 1447, 1680, 1678, 1745, 2252, 2948 cm$^{-1}$.

EXAMPLE 19

Preparation of methyl 5-{(2R)-2-[(3S, 4R)-1-(4-methoxybenzyloxycarbonylmethyl)-3-[(1R)-1-t-butyldimethylsilyloxyethyl]-2-oxo-azetidine-4-yl]propionyl}-4-oxo-3-phenyl-1-oxa-5-azaspiro[5.5]undec-2-en-2-carboxylic acid ester (the General Formula (XI) Compound)

The reaction was performed in the same manner as Example 18 except for using 3.0 g of methyl 5-{(2R)-2-[(3S, 4R)-3-[( 1R)-1-t-butyldimethylsilyloxyethyl]-2-oxo-azetidine-4-yl]propionyl}-4-oxo-3-phenyl-1-oxa-5-azaspiro[5.5]undec-2-en-2-carboxylic acid ester and 4-methoxybenzylbromoacetate instead of allyibromoacetate, thus obtaining 3.23 g of oily desired compound (yield: 83%). $^1$H-NMR(CDCl$_3$, 200 MHz) δ 0.06(s, 6H), 0.86(s, 9H), 1.23(d, J=5.2 Hz, 3H), 1.27(d, J=6.2 Hz, 3H), 1.48–1.68(m, 5H), 2.04–2.21(m, 5H), 3.02 (dd, J=7.4, 2.1 Hz, 1H), 3.52–3.59(m, 1H), 3.63(s, 3H), 3.81(s, 3H), 4.17(dd, J=62.4, 18 Hz, 2H), 4.05–4.17(m, 2H), 5.07(s, 2H), 6.91(m, 2H), 7.20–7.41(m, 7H).

EXAMPLE 20

Preparation of methyl 5-{(2R)-2-[(3S, 4R)-1-(4-nitrobenzyloxycarbonylmethyl)-3-[(1R)-1-t-butyldimethylsilyloxyethyl]-2-oxo-azetidine-4-yl]propionyl}-4-oxo-3-phenyl-1-oxa-5-azaspiro[5.5]undec-2-en-2carboxylic acid ester (the General Formula (XI) Compound)

The reaction was performed in the same manner as Example 18 except for using [4-nitrobenzylbromoacetate was employed instead of] 600 mg of methyl 5-{(2R)-2-[(3S, 4R)-3-[(1R)-1-butyldimethylsilyloxyethyl]-2-oxo-azetidine-4-yl]propionyl}-4-oxo-3-phenyl-1-oxa-5-azaspiro[5.5]undec-2-en-2-carboxylic acid ester and 4-nitrobenzybromoacetate instead of allyibromoacetate, thus obtaining 646 mg of oily desired compound (yield: 84%). $^1$H-NMR(CDCl$_3$, 200 MHz) δ 0.02(s, 6H), 0.82(s, 9H), 1.23(d, J=6.8 Hz, 3H), 1.25(d, J=6.8 Hz, 3H), 1.56–1.78(m, 6H), 2.01–2.36(m, 4H), 3.03(dd, J=7.3, 2.2, 1H), 2.04–2.21(m, 5H), 3.02(dd, J=7.4, 2.1 Hz, 1H), 3.52–3.59(m, 1H), 3.60(s, 3H), 4.17(dd, J=62.4, 18 Hz, 2H), 5.20(s, 2H), 6.91(m, 2H), 7.18'7.37(m, 5H), 7.45(d, J=8.6 Hz, 2H), 8.21(d, J=8.6 Hz, 2H).

EXAMPLE 21

Preparation of allyl (1R, 5R, 6S)-6-[(1R)-1-t-butyldimethylsilyloxyethyl]-1-methyl-2-diphenylphophoryloxy-2-carbapen-2-em-3-carboxylic acid ester (the General Formula (V) Compound)

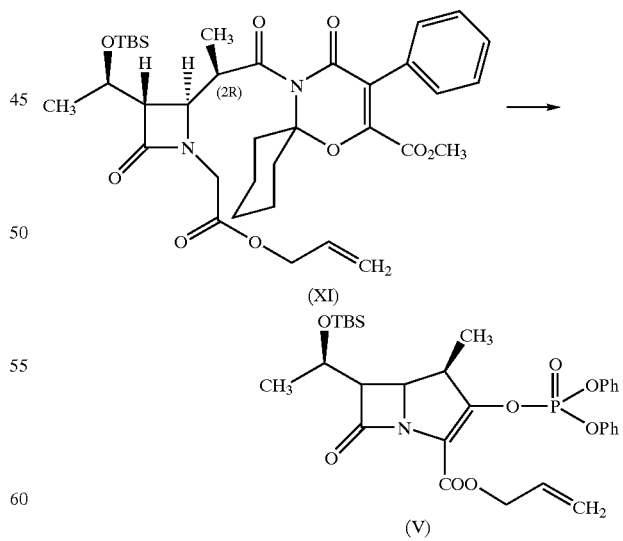

4.89 g of methyl 5-{(2R)-2-[(3S, 4R)-1-allyloxycarbonylmethyl-3-[(1R)-1-t-butyldimethylsilyloxyethyl]-2-oxo-azetidine-4-yl]propionyl}-4-oxo-3-phenyl-1-oxa-5-azaspiro[5.5]undec-2-en-2-carboxylic acid ester was dissolved in 60 ml of anhydrous tetrahydrofuran and cooled down to −45° C. Under the atomosphere of nitrogen gas, 16.9 ml of sodium bis(trimethylsilyl)amide(1 mol of tetrahydrofuran solution) was slowly added to the mixture. With the temperature at −30° C., 1.2 ml of chlorotrimethylsilane was added to the reacting mixture and stirred at the same temperature for 5 minutes. With the slow addition of 2.23 ml of diphenylchlorophosphate, 44 mg of 4-dimethylaminopyridine was further added to the reacting solution and stirred at the temperature of −30~−10° C. for 2 hours. With the addition of phosphate buffer solution (pH= 7.0), the solution was extracted with ethyl acetate two times, dried over MgSO$_4$ and concentrated under reduced pressure. 50 ml of a mixed solution (ethyl acetate: hexane=1:4) was added to the residue and crystallized. After being filtered off, methyl 4-oxo-3-phenyl-1-oxa-5-azaspiro[5.5]undec-2-en-2-carboxylic acid ester in yellow crystal was obtained. This compound, a stereoselective additive, was prepared in the same manner as Preparation example 2 and its recycling can be possible. The remaining solution, so concentrated, was purified on silica gel column chromatography (elute: ethyl acetate: hexane=1:4) to obtain 4.01 g of pure oily desired compound (yield: 91%). $^1$H-NMR(CDCl$_3$, 200 MHz) δ 0.06(s, 6H), 0.87(s, 9H), 1.16(d, J=7.4 Hz, 3H), 1.21(d, J=6.0 Hz, 3H), 3.22(dd, J=6.4, 2.8 Hz, 1H), 3.31–3.52(m, 1H), 4.07–4.21(m, 2H), 4.64(d, J=5.8 Hz, 2H), 5.16(dd, J=10.6, 1.6 Hz, 1H), 5.32(dd, J=17.4, 1.6 Hz, 1H), 5.75–5.94 (m, 1H), 7.17–7.44(m, 10H).

EXAMPLE 22

Preparation of 4-nitrobenzyl(1R, 5R, 6S)-6-[(1R)-1-t-butyidimethylsilyloxyethyl]-1-methyl-2-diphenylphosphoryloxy-2-carbapen-2-em-3-carboxylic acid ester (the General Formula (V) Compound)

The reaction was performed in the same manner as Example 21 using 300 mg of methyl 5-{(2R)-2-[(3S, 4R)-1-(4-nitrobenzyloxycarbonylmethyl)-3-[(1R)-1-t-butyldimethylsilyloxyethyl]-2-oxo-azetidine-4-yl] propionyl}-4-oxo-3-phenyl-1-oxa-5-azaspiro[5.5]undec-2en-2-carboxylic acid ester as starting material, thus obtaining 87 mg of oily desired compound (yield: 32%). $^1$H-NMR(CDCl$_3$, 200 MHz) δ 0.06(s, 6H), 0.85(s, 9H), 1.22(d, J=5.2 Hz, 3H), 1.28(d, J=6.2 Hz, 3H), 3.23–3.33(m, 1H), 3.36–3.48(m, 2H), 5.21–5.39(q, J=10 Hz, 2H), 7.12–7.42(m, 10H), 7.53(d, J=8.6 Hz, 2H), 8.11(d, J=8.4 Hz, 2H).

EXAMPLE 23

Preparation of 4-methoxybenzyl (1R, 5R, 6S)-6-[(1R)-1-t-butyidimethylsilyloxyethyl]-1-methyl-2-diphenylphosphoryloxy-2-carbapen-2-em-3-carboxylic acid ester (the General Formula (V) Compound)

The reaction was performed in the same manner as Example 21 using 323 mg of methyl 5-{(2R)-2-[(3S, 4R)-1-(4-methoxybenzyloxycarbonylmethyl)-3-[(1R)-1-t-butyldimethylsilyloxyethyl]-2-oxo-azetidine-4-yl] propionyl}-4-oxo-3-phenyl-1-oxa-5-azaspiro[5.5]undec-2en-2-carboxylic acid ester as starting material, thus obtaining 222 mg of oily desired compound (yield: 85%).

$^1$H-NMR(CDCl$_3$, 200 MHz) δ 0.01(s, 6H), 0.82(s, 9H), 1.12(d, J=7.4 Hz, 3H), 1.17(d, J=6.0 Hz, 3H), 3.24–3.49(m, 1H), 3.72(s, 3H), 4.01–4.22(m, 2H), 7.08–7.41(m, 12H).

EXAMPLE 24

Preparation of (2R)-2-[(3S, 4R)-3-[(1R)-t-butyidimethylsilyloxyethyl]-2-oxo-azetidine-4-yl] propionic acid (the General Formula (IV) Compound)

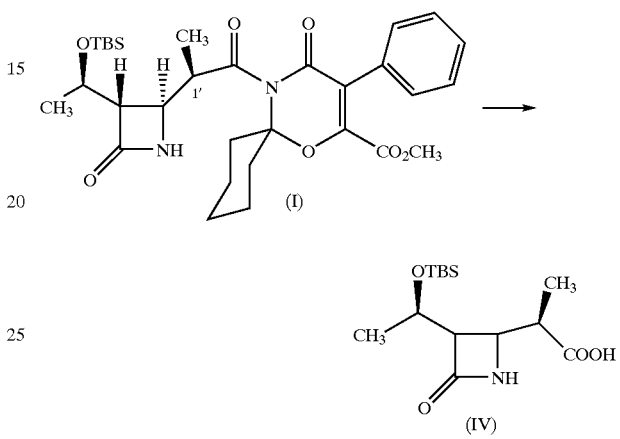

388 mg of methyl 5-{(2R)-2-[(3S, 4R)-3-[(1R)-1-t-butyldimethylsilyloxyethyl]-2-oxo-azetidine-4-yl] propionyl}-4-oxo-3-phenyl-1-oxa-5-azaspiro[5.5]undec-2-en-2-carboxylic acid ester, so prepared by Example 10, was dissolved in 10 ml of anhydrous tetrahydrofuran and 0.34 ml of water and cooled down to 0° C. 0.6 ml of 30% hydrogen peroxide and 56 mg of lithium hydroxide were added to the reacting solution. The solution was stirred at the same temperature for 1 hour and then, 4 ml of 1.5 normal sodium sulfite solution was added to the reacting solution. After tetrahydrofuran was concentrated under reduced pressure, the crystals formed from the remaining solution was being filtered off to obtain methyl 4-oxo-3-phenyl-1-oxa-5-azaspiro[5.5]undec-2-en-2-carboxylic acid ester. After the remaining solution was washed with chloroform and pH was also adjusted to about 1 using 10% hydrochloric acid, the solution was extracted with ethyl acetate, dried over MgSO$_4$ and concentrated under reduced pressure. The residue was crystallized with ethyl acetate and hexane to obtain 144 mg of desired compound in white solid form (yield: 73%). ml 143–1460° C.

Through the preparation of the general formula (I) compound using the general formula (III) compound as an stereoselective additive of this invention, the stereoisomers only having β-methyl group in 1'-position of the general formula (I) compound may be made available in an effective manner.

The existing literature (*Tetrahedron*, Vol. 52, No. 2 pp. 331–375. 1996) has disclosed a process of preparing the intermediate of β-methylcarbapenem antibiotics corresponding to the general formula (I) of this invention using a stereoselective additive.

The following table 4 summarized the ratios of β-isomer generated, when zinc powder was used as an easily handled reagent.

TABLE 4

Ratios of β-isomer of the general formula (V) compound generated by reacting the general formula (II) compound with diverse stereoselective additives

| Stereoselective additive | Reagent | Ratio of β:α (1'methyl) | Developer |
|---|---|---|---|
| 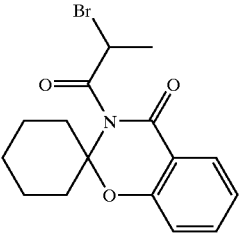 | Zinc powder | 92:8 | Tanabe of Japan |
| 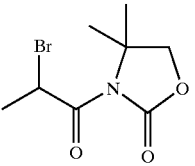 | Zinc powder | 79:21 | Sagami of Japan |
| 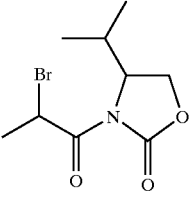 | Zinc powder | 91:9 | Sagami of Japan |
| 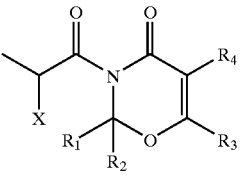 | Zinc powder | 98:2 (Example 11) | This invention |

The highest ratio of β-isomer according to this invention was 98:2 (Example 11), while the lowest ratio was 92:8 (Example 13). The average ratio of β-isomer was 96:4.

The above table 4 indicated that the ratio of β-isomer of Tanabe and Sagami was 92:8, 79:21 and 91:9, respectively.

In comparison, it was found that a higher ratio of β-isomer was achieved.

Further, this invention has an advantage of recycling the by-product of the general formula (III) compound, a stereoselective additive, after recovery process during the process of preparing the general formula (V) compound, a final intermediate of carbapenem antibiotic from the general formula (I) compound.

What is claimed is:
1. An azetidinone compound of the formula (I):

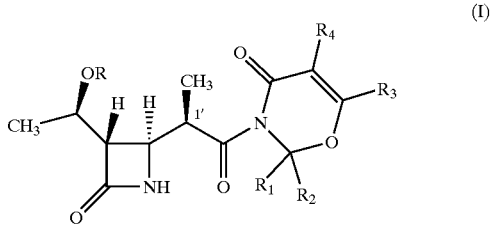

(I)

wherein R is a hydrogen atom or a hydroxy protecting group
$R_1$ and $R_2$ are independently $C_1$–$C_{15}$ alkyl, benzyl or cyclized together with the carbon atom to which they are attached to form a 5 or 6-membered cyclic hydrocarbon or a heterocyclic radical having one or two hetero ring atoms, said hetero ring atoms being selected from the group consisting of O and S; $R_3$ is lower alkyl or —COO(lower alkyl); $R_4$ is phenyl or phenyl substituted with halogen atom, a lower alkoxy or nitro; and the methyl group in 1' position is in the R configuration.

2. The compound according to claim 1, wherein R is t-butyldimethylsilyl; $R_1$ and $R_2$ are independently $C_1$–$C_6$ alkyl, benzyl or cyclized together with the carbon atom to which they are attached to form a 5 or 6-membered cyclic hydrocarbon; $R_3$ is —COO(lower alkyl); and $R_4$ is phenyl or phenyl substituted with halogen atom, a lower alkoxy or nitro.

3. The compound according to claim 1, wherein said compound of the formula (I) is methyl 5-{(2R)-2-[(3S,4R)-3-[( 1R)-1-t-butyldimethylsilyloxyethyl]-2-oxoazetidine-4-yl]propionyl}-4-oxo-3-phenyl-1-oxa-5-azaspiro[5,5]undec-2-en-2-carboxylic acid ester.

4. A process for preparing a compound of the formula (I), which comprises reacting a compound of the formula (II) with a compound of the formula (III):

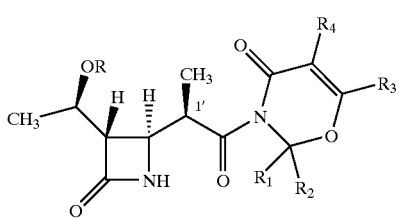
(I)

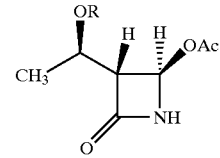
(II)

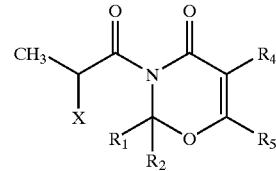
(III)

wherein R, $R_1$, $R_2$, $R_3$, and $R_4$ are the same as defined in claim 1 and X is a halogen atom.

5. The process according to claim 4, wherein R is t-butyldimethylsilyl; $R_1$ and $R_2$ are cyclized together with the carbon atom to which they are attached to form a cyclohexyl ring; $R_3$ is methoxycarbonyl; $R_4$ is phenyl; and X is bromo.

* * * * *